US008206969B2

(12) United States Patent
Hauer et al.

(10) Patent No.: US 8,206,969 B2
(45) Date of Patent: Jun. 26, 2012

(54) CALB MUTEINS AND THEIR USE

(75) Inventors: Bernhard Hauer, Fussgönheim (DE);
Cecilia Kvarnström Branneby,
Stockholm (SE); Rolf Schmid, Stuttgart
(DE); Steffen Maurer, Dirmstein (DE);
Peter Trodler, Ingelheim (DE); **Danni
Liu, Stuttgart (DE); Monika Müller**,
Aachen (DE)

(73) Assignee: BASF SE, Ludwigshafen (DE)

( * ) Notice: Subject to any disclaimer, the term of this patent is extended or adjusted under 35 U.S.C. 154(b) by 120 days.

(21) Appl. No.: 12/809,118

(22) PCT Filed: Dec. 18, 2008

(86) PCT No.: PCT/EP2008/067811
§ 371 (c)(1),
(2), (4) Date: Jun. 18, 2010

(87) PCT Pub. No.: WO2009/080676
PCT Pub. Date: Jul. 2, 2009

(65) Prior Publication Data
US 2010/0273223 A1 Oct. 28, 2010

(30) Foreign Application Priority Data
Dec. 20, 2007 (EP) .................................. 07150242

(51) Int. Cl.
*C12N 9/84* (2006.01)
(52) U.S. Cl. ...................................................... 435/230
(58) Field of Classification Search ........................ None
See application file for complete search history.

(56) References Cited

U.S. PATENT DOCUMENTS

| 6,596,520 | B1 | 7/2003 | Friedrich et al. |
| 7,531,331 | B2 | 5/2009 | Hauer et al. |
| 2005/0181472 | A1 | 8/2005 | Hauer et al. |
| 2006/0286651 | A1 | 12/2006 | Kazlauskas et al. |
| 2010/0068760 | A1 | 3/2010 | Breuer et al. |
| 2010/0196970 | A1 | 8/2010 | Hauer et al. |

FOREIGN PATENT DOCUMENTS

| EP | 0 892 044 A2 | 1/1999 |
| EP | 1069183 A2 | 1/2001 |
| WO | WO-02/18560 A2 | 3/2002 |
| WO | WO-2004/024954 A1 | 3/2004 |

OTHER PUBLICATIONS

Witkowski, A., et al, "Conversion of a β-Ketoacyl Synthase to a Malonyl Decarboxylase by Replacement of the Active-Site Cysteine with Glutamine", Biochemistry, 1999, vol. 38, pp. 11643-11650.
Itakura, K., et al., "Synthesis and Use of Synthetic Oligonucleotides", Ann. Rev. Biochem., 1984, vol. 53, pp. 323-356.
Kuchner, O., et al., "Directed Evolution of Enzyme Catalysts", TIBTECH, 1997, vol. 15, pp. 523-530.
Narang, S. A., et al., "DNA Synthesis", Tetrahedron, 1983, vol. 39, No. 1, pp. 3-22.
Pearson, W. R., et al., "Improved Tools for Biological Sequence Comparison", Proc. Natl. Acad. Sci. USA, 1988, vol. 85, pp. 2444-2448.
Reetz, M. T., et al., "Superior Biocatalysts by Directed Evolution", Topics in Current Chemistry, 1999, vol. 200, pp. 31-57.
Zhao, H., et al., "Methods for Optimizing Industrial Enzymes by Directed Evolution", Chapter 49 in "Manual of Industrial Microbiology and Biotechnology", 1999, pp. 597-604.
Delagrave, S., et al., "Recursive Ensemble Mutagenesis", Protein Engineering, 1993, vol. 6, No. 3, pp. 327-331.
Arkin, A. P., et al., "An Algorithm for Protein Engineering: Simulations of Recursive Ensemble Mutagenesis", Proc. Natl. Acad. Sci. USA, 1992, vol. 89, pp. 7811-7815.
Ike, Y., et al., "Solid Phase Synthesis of Polynucleotides. VIII. Synthesis of Mixed Oligodeoxyribonucleotides by the Phosphotriester Solid Phase Method", Nucleic Acids Research, 1983, vol. 11, No. 2, pp. 477-488.
Itakura, K., et al., "Expression in *Escherichia coli* of a Chemically Synthesized Gene for the Hormone Somatostatin", Science, 1977, vol. 198, pp. 1056-1063.
Butinol Esterase Mutant Experimental Data—"Expression of the Truncated 335 AA Butynol Esterase", Annex 1, 2006.
Butinol Esterase Mutant Experimental Data—"Expression of the Truncated 335 AA Butynol Esterase", Annex 2, 2006.
Chica, R. A., et al., "Semi-Rational Approaches to Engineering Enzyme Activity: Combining the Benefits of Directed Evolution and Rational Design", Curr. Opin. Biotechnol., 2005, vol. 16, No. 4, pp. 378-384.
Seffernick, J. L., et al., "Melamine Deaminase and Atrazine Chlorohydrolase: 98 Percent Identical but Functionally Different", J. Bacteriol., 2001, vol. 183, No. 8, pp. 2405-2410.
"*Pseudomonas fluorescens* Alcohol Dehydrogenase (Adhf1), Putative Flavin-Binding Monooxygenase, Lactone-Specific Esterase (Estf1), Putative Alkane 1-Monooxygenase, Putative Activator of Alkane Oxidation ORF3, and Putative Activator of Alkane Oxidation ORF2 Genes, Complete CDS; and Putative Outer Membrane Protein Gene, Partial CDS,", GenBank Accession No. AF090329, Aug. 15, 2002.
Faraldos, J., et al., "Biocatalysis in Organic Synthesis. 9. Highly Enantioselective Kinetic Resolution of Secondary Alcohols Catalyzed by Acylase", Synlett, 1997, vol. 4, pp. 367-370.
Khalameyzer, V., et al., "Screening, Nucleotide Sequence, and Biochemical Characterization of an Esterase from *Pseudomonas fluorescens* with High Activity towards Lactones", Applied and Environmental Microbiology, 1999, vol. 65, No. 2, pp. 477-482.
Manco, G., et al., "Overexpression and Properties of a New Thermophilic and Thermostable esterase from *Bacillus acidocaldarius* with Sequence Similarity to Hormone-Sensitive Lipase Subfamily", Biochem. J., 1998, vol. 332, pp. 203-212.
Peist, R., et al., "Characterization of the *aes* Gene of *Escherichia coli* Encoding an Enzyme with Esterase Activity", Journal of Bacteriology, 1997, vol. 179, No. 24, pp. 7679-7686.

(Continued)

Primary Examiner — Tekchand Saidha
Assistant Examiner — Md. Younus Meah
(74) Attorney, Agent, or Firm — Connolly Bove Lodge & Hutz, LLP

(57) ABSTRACT

A protein having acrylation activity having a polypeptide sequence derived from SEQ ID NO: 1 or NO:2 by introducing at least one of the following amino acid substitutions: L278A, L278V, W104F, T42A, S47A.

5 Claims, 1 Drawing Sheet

OTHER PUBLICATIONS

Quyen, D. T., et al., "A Novel Esterase from *Ralstonia* sp. M1: Gene Cloning, Sequencing, High-Level Expression and Characterization", Protein Expression and Purification, 2007, vol. 51, pp. 133-140.

Yang, H., et al., "The Use of Vinyl Esters Significantly Enhanced Enantioselectivities and Reaction Rates in Lipase-Catalyzed Resolutions of Arylaliphatic Carboxylic Acids", Journal of Organic Chemistry, 1999, vol. 64, No. 5, pp. 1709-1712.

Balkenhohl, F., et al., "Optisch aktive Amine durch Lipase-katalysierte Methoxyacetylierung", Journal für praktische Chemie Chemiker-Zeitung, 1997, vol. 339, pp. 381-384 (Article in German, see English Language Abstract).

Gudelj, M., et al., "Novel *Rhodococcus* Esterases by Genetic Engineering", Journal of Molecular Catalysis B: Enzymatic, 1998, vol. 5, pp. 261-266.

Nakamura, K., et al., "Lipase-Catalyzed Kinetic Resolution of 3-Butyn-2-ol", Tetrahedron: Asymmetry, 1998, vol. 9, pp. 4429-4439.

"Hydrolase, alpha/beta fold family", NCBI Genbank Accession No. Q2T897, Oct. 31, 2006.

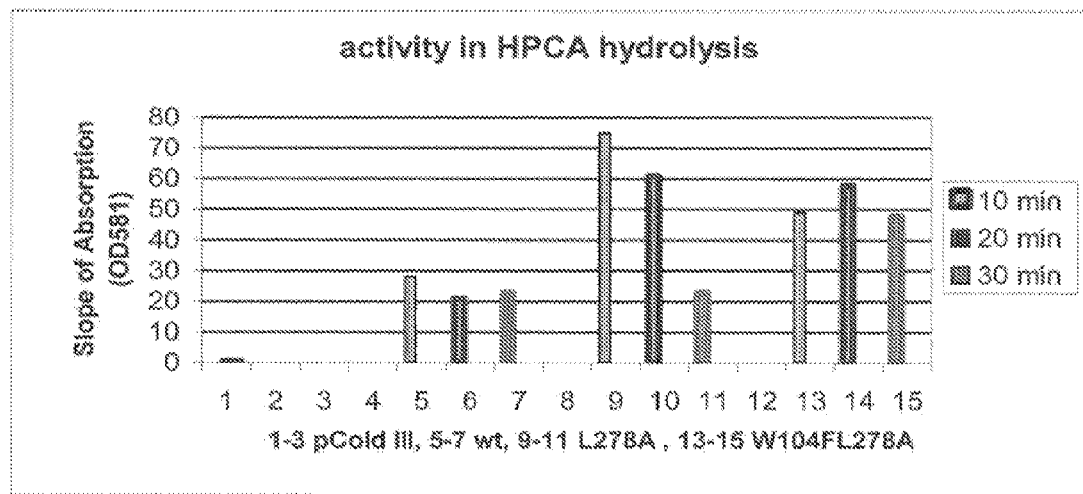

SEQUENCE LISTING

<160> NUMBER OF SEQ ID NOS: 6

<210> SEQ ID NO 1
<211> LENGTH: 317
<212> TYPE: PRT
<213> ORGANISM: Candida antarctica

<400> SEQUENCE: 1

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
```

```
            225                 230                 235                 240
Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315

<210> SEQ ID NO 2
<211> LENGTH: 317
<212> TYPE: PRT
<213> ORGANISM: Candida antarctica

<400> SEQUENCE: 2

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Ala Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
```

```
                    290                 295                 300
Ala Val Gly Lys Arg Thr Cys Ser Gly Ile Val Thr Pro
305                 310                 315
```

<210> SEQ ID NO 3
<211> LENGTH: 33
<212> TYPE: DNA
<213> ORGANISM: Artificial sequence
<220> FEATURE:
<223> OTHER INFORMATION: synthetic mutagenesis primer
<220> FEATURE:
<221> NAME/KEY: mutation
<222> LOCATION: (10)..(10)
<223> OTHER INFORMATION: codon aa 278
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: mutation
<222> LOCATION: (11)..(11)
<223> OTHER INFORMATION: codon aa 278
<220> FEATURE:
<221> NAME/KEY: mutation
<222> LOCATION: (12)..(12)
<223> OTHER INFORMATION: codon aa 278

<400> SEQUENCE: 3
gctgcgctcn nkgcgccggc ggctgcagcc atc                                33

<210> SEQ ID NO 4
<211> LENGTH: 33
<212> TYPE: DNA
<213> ORGANISM: Artificial sequence
<220> FEATURE:
<223> OTHER INFORMATION: synthetic mutagenesis primer
<220> FEATURE:
<221> NAME/KEY: mutation
<222> LOCATION: (12)..(12)
<223> OTHER INFORMATION: codon aa 278
<220> FEATURE:
<221> NAME/KEY: mutation
<222> LOCATION: (13)..(13)
<223> OTHER INFORMATION: codon aa 278
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: mutation
<222> LOCATION: (14)..(14)
<223> OTHER INFORMATION: codon aa 278

<400> SEQUENCE: 4
gccgccggcg cmnngagcgc agccgcggcg acc                                33

<210> SEQ ID NO 5
<211> LENGTH: 38
<212> TYPE: DNA
<213> ORGANISM: Artificial sequence
<220> FEATURE:
<223> OTHER INFORMATION: synthetic mutagenesis primer
<220> FEATURE:
<221> NAME/KEY: mutation
<222> LOCATION: (20)..(20)
<223> OTHER INFORMATION: n is part of codon aa 104
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: mutation
<222> LOCATION: (21)..(21)
<223> OTHER INFORMATION: n is part of codon aa 104

```
<220> FEATURE:
<221> NAME/KEY: mutation
<222> LOCATION: (22)..(22)
<223> OTHER INFORMATION: k is part of codon aa 104

<400> SEQUENCE: 5
caagcttccc gtgctcaccn nktcccaggg tggtctgg                              38

<210> SEQ ID NO 6
<211> LENGTH: 38
<212> TYPE: DNA
<213> ORGANISM: Artificial sequence
<220> FEATURE:
<223> OTHER INFORMATION: synthetic mutagenesis primer
<220> FEATURE:
<221> NAME/KEY: misc_feature
<222> LOCATION: (18)..(19)
<223> OTHER INFORMATION: n is a, c, g, or t

<400> SEQUENCE: 6
ccagaccacc ctgggamnng gtgagcacgg gaagcttg                              38
```

CALB MUTEINS AND THEIR USE

RELATED APPLICATIONS

This application is a national stage application (under 35 U.S.C. §371) of PCT/EP2008/067811, filed Dec. 18, 2008, which claims benefit of European application 07150242.1, filed Dec. 20, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_01031. The size of the text file is 8 KB, and the text file was created on Jun. 17, 2010.

The invention relates to novel proteins having lipase activity, to nucleic acid sequences coding therefore, to expression cassettes, vectors and recombinant microorganisms; to methods for preparing said proteins and to the use thereof for enzymatic, in particular ester hydrolysis or transesterification of organic esters.

Lipases are hydrolases which can be employed in industrial processes for synthesizing optically active organic compounds and which are characterized by high substrate specificity.

Lipases (EC 3.1.1.3) are the enzymes most frequently used in catalysis. They catalyze predominantly hydrolysis, esterification and transesterification reactions. Within the lipases *Candida antarctica* lipase B (CALB) (EC 3.1.1.3) is the most important lipase in industrial applications for chemical synthesis. CALB is a serine hydrolase with an α/β hydrolase fold, which is conserved within the family of lipases, and a catalytic triad consisting of Ser, His and Asp. CALB is a lipase with special properties compared to many other lipases. CALB has no lid covering the entrance to the active site and no hydrophobic patch on the surface like many other lipases and shows no interfacial activation. The catalytic serine in lipases is usually identified by the conserved sequence GXSXG, which is exchanged to TXSXG in CALB.

CALB is a highly versatile catalyst with activity towards a wide range of different substrates and shows high specificity and stereoselectivity towards many compounds. CALB is a useful enzyme with high enantioselectivity for hydrolysis in water and esterification in organic solvents. Its high stability, stereoselectivity and activity in organic solvents and even at elevated temperature make CALB an ideal catalyst for chemical conversions even on industrial scale.

Acrylation is a means to introduce cross-linking functionality into target compounds. Traditional chemical processes for producing acrylate esters employ high temperatures frequently leading to polymerization of acrylic double bonds. To avoid these unwanted reactions polymerization inhibitors and acid catalysts have been introduced [Ohrui, 1975] allowing for reactions at 80 to 100° C. Still enzymatic processes conducted at moderate temperature might be beneficial in acrylation reactions as additives can be omitted, energy saved and product quality and purity improved. Selectivity of enzymes is an advantage if there are several reactive functionalities (hydroxyls, amines, thiols) in the molecule of interest.

However, the lipases disclosed in the prior art do not catalyze the transesterification reactions with a yield high enough for a technical process. Especially the acrylation e.g. the transesterification of acrylic ester with hydroxypropylcarbamate is not sufficient with the CALB enzyme.

It is an object of the present invention to provide lipases which show better enzymatic activities such as yield for the above-mentioned acrylation reaction.

We have found that this object is achieved, surprisingly, by providing proteins having acrylation activity having a polypeptide sequence derived from SEQ ID NO: 1 by introducing at least one of the following amino acid substitutions:
L278A, L278V, W104F, T42A, S47A.

The proteins according to the invention have acrylation activity. This means that the proteins are able to catalyze the following reaction:

Transesterification reaction of acrylic ester with hydroxypropylcarbamates catalyzed by CALB and CALB-Muteins (Abbreviations hpc for the hydroxypropylcarbamate regio- and stereoisomers and hpca for the acrylated hpc are used).

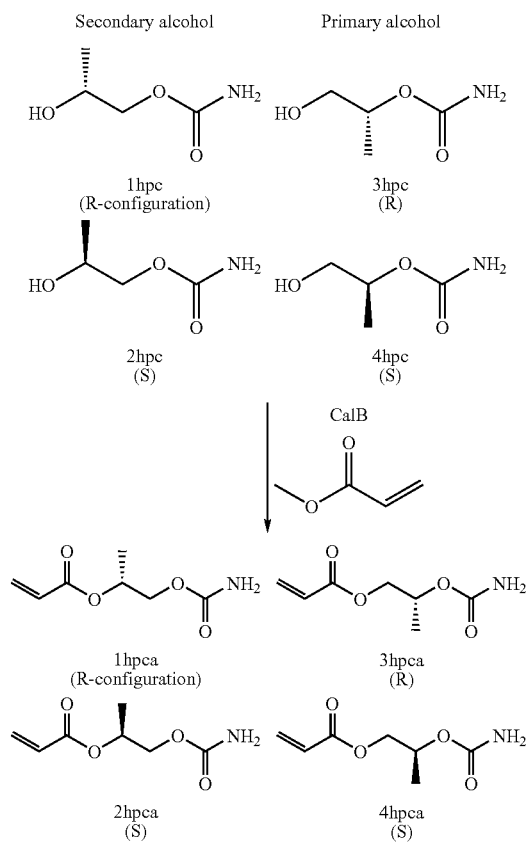

For the sake of simplicity, the abovementioned proteins are denoted as CALB-Muteins.

The lipase B of *Candida antarctica* (CALB) has the known polypeptide sequence SEQ ID NO:1. We have found in addition to SEQ ID NO:1 another polypeptide sequence in *Candida antarctica* samples which have lipase activity. This second sequence is disclosed as SEQ ID NO:2. The proteins according to the invention are derived from the CALB by introducing at least one amino acid substitution into the SEQ ID NO:1 or NO:2 (CALB-muteins), at the positions 278 and/or 104 and/or 42 and/or 47.

A preferred CALB-mutein is one which is derived from SEQ ID NO:1 or NO:2 by substitution of Leucine (L) at position 278 by Alanine (A) (L278A) or Valine (V) (L278V).

Another preferred CALB-mutein is one which is derived from SEQ ID NO:1 or NO:2 by substitution of Tryptophane (W) at position 104 by Phenylalanine (F) (W104F).

Another preferred CALB-mutein is one which is derived from SEQ ID NO:1 or NO:2 by substitution of Serine (S) at position 47 by Alanine (A) (S47A).

Another preferred CALB-mutein is one which is derived from SEQ ID NO:1 or NO:2 by substitution of Serine (T) at position 42 by Alanine (A) (T42A).

Another preferred CALB-mutein is one which is derived from SEQ ID NO:1 or NO:2 by substitution of Leucin (L) at position 278 by Alanine (A) (L278A) and by substituting of Threonine (T) at position 42 by Alanine (A) (T42A).

Another preferred CALB-mutein is one which is derived from SEQ ID NO:1 or NO:2 by substitution of Leucin (L) at position 278 by Valine (V) (L278V) and by substituting of Threonine (T) at position 42 by Valine (V) (T42V).

Another preferred CALB-mutein is one which is derived from SEQ ID NO:1 or NO:2 by substitution of Leucine (L) at position 278 by Alanine (A) (L278A) or Valine (V) and by substitution of Serine (S) at position 47 by Alanine (A) (S47A).

Another preferred CALB-mutein is one which is derived from SEQ ID NO:1 or NO:2 by substitution of Leucine (L) at position 278 by Alanine (A) (L278A) and by substitution of Tryptophane (W) at position 104 by Phenylalanine (F) (W104F).

Another preferred CALB-mutein is one which is derived from SEQ ID NO:1 or NO:2 by substitution of Leucine (L) at position 278 by Alanine (A) (L278A) or Valine (V) (L278V) and by substituting of Tryptophane (W) at position 104 by Phenylalanine (F) (W104F) and by substituting of Serine (S) at position 47 by Alanine (A) (S47A).

The above-mentioned CALB-muteins may have—in addition to the amino acid substitutions at positions 42 and/or 47 and/or 104 and/or 278—further amino acid substitutions or deletions or insertions in other positions of the polypeptide compared to SEQ ID NO:1 or NO:2 as long as the acrylation activity is not reduced to less than 50% of the activity of the CALB muteins without these further amino acid substitutions or deletions or insertions.

Another aspect of the invention is polynucleotide sequences coding for the CALB-muteins disclosed above. These polynucleotide sequences can be retranslated from the polypeptide sequence by computer programs using the genetic code.

Preferably the polynucleotide sequence is adapted to the codon usage of the host organism which is chosen for the expression of the polynucleotide.

Another aspect of the invention is expression cassettes comprising the polynucleotide sequences coding for the CALB-muteins. Such expression cassettes usually containing regulatory elements such as promoters, terminators in combination with the polynucleotide sequences coding for the CALB-muteins, which allow an efficient expression of the CALB-mutein-genes.

The invention also relates to expression cassettes including at least one inventive polynucleotide which is operatively linked to regulatory nucleic acid sequences. Preferably, a promoter sequence is located 5' upstream of the polynucleotide of the invention and facilitates in this way controlled expression of the CALB-muteins. Particularly preferably, a terminator sequence and also, where appropriate, further customary regulatory elements are located 3' downstream of the polynucleotide of the invention, each of them operatively linked to the sequence encoding CALB-muteins. Operative linkage means the sequential arrangement of promoter, coding sequence, terminator and, where appropriate, further regulatory elements such that each of the regulatory elements can fulfill its function before, during or after expression of the coding sequence as intended. Examples of further operatively linkable sequences are targeting sequences and also translation amplifiers, enhancers, polyadenylation signals and the like. Further useful regulatory elements include selectable markers, reporter genes, amplification signals, replication origins and the like.

Examples of useful promoters are: cos, tac, trp, tet, trp-tet, lpp, lac, lpp-lac, laciq, T7, T5, T3, gal, trc, ara, SP6, .lambda.-PR or .lambda.-PL promoter which are advantageously used in Gram-negative bacteria; and also the Gram-positive promoters amy and SPO2, the yeast promoters ADC1, MFa, AC, P-60, CYC1, GAPDH or the plant promoters CaMV/35S, SSU, OCS, lib4, usp, STLS1, B33, nos or the ubiquitin promoter or phaseolin promoter. Particular preference is given to using inducible promoters such as, for example, light- and in particular temperature-inducible promoters such as the P.sub-.rP.sub.1 promoter.

In principle it is possible to use all natural promoters with their regulatory sequences. Moreover, it is also advantageous and possible to use synthetic promoters.

Said regulatory sequences ought to facilitate specific expression of the nucleic acid sequences and protein expression. Depending on the host organism, this can mean, for example, that the gene is expressed or overexpressed only after induction, or that it is expressed and/or overexpressed immediately.

In this context, it is possible for the regulatory sequences or factors to positively influence and thereby increase or decrease expression. Thus, the regulatory elements can be advantageously enhanced at the transcription level by using strong transcription signals such as promoters and/or enhancers. Aside from this, however, it is also possible to enhance translation by, for example, increasing the mRNA stability.

An expression cassette of the invention is produced by fusion of a suitable promoter with a suitable polynucleotide encoding CALB-muteins and also with a terminator or polyadenylation signal. For this, customary recombination and cloning techniques are used, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The invention also relates to recombinant vectors for transforming eukaryotic and prokaryotic hosts carrying a polynucleotide of the invention or an expression cassette of the invention. Said vectors allow CALB-mutein expression in a suitable host organism. Vectors are well known to the skilled worker and can be found, for example, in "Cloning Vectors" (Pouwels P. H. et al., eds., Elsevier, Amsterdam-New York-Oxford, 1985). Vectors mean, in addition to plasmids, also all other vectors known to the skilled worker such as, for example, phages, viruses such as SV40, CMV, baculovirus and adenovirus, transposons, IS elements, phasmids, cosmids, and linear or circular DNA. These vectors can be replicated autonomously or chromosomally in the host organism.

With the aid of the vectors of the invention it is possible to produce recombinant microorganisms which, for example, have been transformed with at least one vector of the invention and can be employed for producing recombinant CALB-muteins. Advantageously, the above-described recombinant expression cassettes of the invention are introduced as part of an expression vector into a suitable host system and expressed. Preference is given here to familiar cloning and transfection methods known to the skilled worker, in order to express said nucleic acids in the particular expression system. Suitable systems are described, for example, in Current Protocols in Molecular Biology, F. Ausubel et al., eds., Wiley Interscience, New York 1997.

Host organisms which are suitable for transformation with vectors of the invention are in principle all organisms facilitating expression of the inventive polynucleotides, of allelic variants, functional equivalents or derivatives thereof. Host organisms mean, for example, bacteria, fungi, yeasts, plant or animal cells. Preferred organisms are bacteria such as those of the genera *Escherichia, Streptomyces, Bacillus* or *Pseudomonas*, eukaryotic microorganisms such as *Saccharomyces cerevisiae, Aspergillus*, higher eukaryotic cells from animals or plants, for example Sf9 or CHO cells. Successfully transformed organisms can be selected through marker genes which are likewise contained in the vector or in the expression cassette. Examples of such marker genes are genes for antibiotics resistance and for enzymes catalyzing a staining reaction causing staining of the transformed cells. Said cells can then be selected by means of automated cell sorting. Organisms which have been successfully transformed with a vector and which carry an appropriate antibiotics resistance gene can be selected on media or substrates containing appropriate antibiotics. Marker proteins presented at the cell surface can be used for selection by means of affinity chromatography.

Another aspect of the invention is a process for transesterification, wherein a stereoisomer mixture of an optically active alcohol of the formula II is contacted with an ester of the formula I in the presence of a protein as claimed in claim 1 and the acrylated mixture of alcohols of the formula III is obtained from the reaction medium

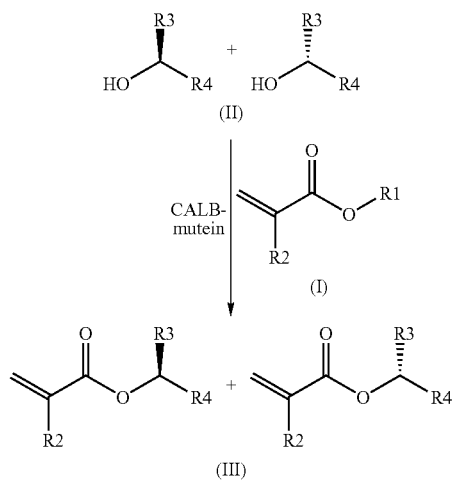

With $R^1 = C_1\text{-}C_6$ Alkyl
$R^2 = H, CH_3$
$R^3, R^4 = C_1\text{-}C_6$ Alkyl, where one or two H-atoms can be substituted by OH, SH, $NH_2$, F, Cl, Br, J, CN, —O—$CONH_2$, —O—COOH, —$OCOOR^1$, or aryl, with the proviso that $R^3 \neq R^4$ Preferred esters of the formula I are those where $R^2 = H$ and $R^1 = $ Methyl, Ethyl, n-Propyl, iso-Propyl, n-Butyl.

Preferred optically active alcohols of formula II are those where $R^3 = $ Methyl and $R^4 = CH_2OCONH_2$ or $R^3 = $ Methyl and $R^4 = C_4H_9$. A preferred embodiment of the process uses a mixture of regio- and stereoisomers of hydroxypropylcarbamate.

The process is carried out at temperatures between 5 and 60° C., preferably between 30 and 50° C.

The CALB-muteins used in the process according to the invention can be used either as an enzyme solution or in immobilized form. Preferred is the immobilization of the enzyme with a carrier made from organic or inorganic materials.

Immobilization of enzymes is known in the art (Roger A. Sheldon, Enzyme Immobilization: The Quest for Optimum Performance, Advanced Synthesis & Catalysis, Vol: 349, NO: 8-9, 1289-1307, 2007; and Juta Kobayashi, Yuichiro Mori and Shū Kobayashi, Chem. Commun., 2006, 4227-4229)

The process according to the invention can be carried out in a solvent, e.g. in an organic solvent such as an ether or in a mixture of organic solvent and water, which can also be a two-phase-system. However, it is also possible to carry out the reaction without a additional solvent.

In order to achieve a high yield in the transesterification reaction the alcohol of the acrylateester of formula I can be removed by known methods such as distillation, molecular sieves etc. Preferred is the distillation.

Experimental Section

Chemicals:

Acrylic esters, solvents and chemicals were purchased from Fluka (Buchs, CH), unless stated otherwise. MP 1000 (Akzo, Germany), HP20 and HP2MG (Mitsubishi Chemical), Hydroxypropylcarbamate (Carbalink).

Strains and Plasmids:

*E. coli* Origami B cells (Δara-leu7697 ΔlacX74 ΔphoAPvull phoR araD139 ahpC galE galK rpsL F'[lac+(laclq)pro] gor522::Tn10 (TcR) trxB::kan) were purchased from Novagen (Darmstadt, Germany). The plasmid pCold III, which contains a resistance marker (Ampicillin) and utilizes the cspA promoter, was purchased from Takara (Ostu, Japan). Downstream of the cspA promoter, a lac operator was inserted making the expression strictly controlled by IPTG. The vector pPICZαA, using the methanol inducible 5'AOX1 promoter and Zeocin as resistance marker, was purchased from Invitrogen. The construct pPICZαA/calB used for expression of CalB in *Pichia pastoris* X33 (Invitrogen, Paisley, UK) has been described previously. The analysis of the calB gene amplified from genomic DNA of *C. antarctica* revealed two alterations from the published calB sequence (CAA83122.1=SEQ ID NO:1) on amino acid level (T57A, A89T) This sequence is named SEQ ID NO:2.

Expression of CALB in Shake Flasks:

For expression of CALB in *Pichia pastoris* the vector pPICZαA was used. Growth and expression conditions were essentially as described in the pPICZαA manual (Invitrogen, Paisley, UK). After six days of protein expression, the cells were removed by centrifugation. >50% pure CALB was secreted to the supernatant. Peptides were removed from the supernatant by ultrafiltration using VivaSpin (VivaScience, 10 kDa MWCO) concentrators.

Site-Directed Mutagenesis

Starting from the sequence information of CALB, mutations at positions T42, S47, W104 and L278 were introduced into the calB gene by Quikchange PCR (Stratagene) according to the manufacturer's protocol. The changes in the plasmid construct pPICZαA/calB were verified by DNA sequencing.

Multi Site Saturation Mutagenesis

In order to create a library by saturation mutagenesis partially degenerated primers were used. Primers for saturation mutagenesis in one amino acid position were designed using NNK as codon for the degenerated position. The sequence of the L278X primers was: 5'-GCTGCGCTCnnkGCGCCG- GCGGCTGCAGCCATC-3', 5'-GCCGCCGGCGCmn-nGAGCGCAGCCGCGGCGACC-3'; the sequence of the W104X primers was: 5'-CAAGCTTCCCGTGCTCACCnn-kTCCCAGGGTGGTCTGG-3', 5'-CCAGACCACCCTGG-GAmnnGGTGAGCACGGGAAGCTTG-3'. Two methods were utilized in saturation mutagenesis. One was sequential introduction of mutations (data not shown) by QuikChange site-directed mutagenesis according to the manufacturer's instructions. The other method employed QuikChange® Multi Site-Directed Mutagenesis Kit allowing for one-step introduction of several mutations.

CALB Expression in Microtiter Plates

Expression of CALB in the *E. coli* cytoplasm was based on the pColdIII vector system (TAKARA BIO INC., Japan). The purified PCR product was used to transform Origami B cells by electroporation. 50 µl cell suspension was plated on LBamp-tributyrine plates. After overnight cultivation at 37° C. colonies showing halos and therefore producing an active lipase were picked into 96-well MTPs containing LB-media supplemented with 100 µg ml$^{-1}$ ampicillin. Lipase expression and cell lysis were performed as described previously [Liu, 2006]. Furthermore, in order to compare mutant proteins' activities, three rows of standards were cultivated in each MTP: Origami B transformed with pColdIII (empty vector), pColdIII/calb_wt and pColdIII/calb_L278A (Table 4).

General Activity Assay: Hydrolysis of Tributyrine

Measurements of the activity of CALB and mutants thereof in the hydrolysis of tributyrine were done by the pH-stat method. 50 µl of the supernatant of the expression in *Pichia pastoris* were added at 30° C. and pH 7.5 to 20 ml tributyrine emulsion (5% tributyrine, 2% gum arabicum in water). The pH was kept constant by titration with 0.01 N NaOH. NaOH consumption was recorded.

Hydrolysis Assay for Hpca

The high-throughput activity assay is based on hydrolysis of the target product (acrylated hydroxypropylcarbamate (HPCA) and simultaneous spectrophotometrical detection of the protons released in this reaction using the pH-indicator bromocresol purple. This indicator displays a color change from pH 6.8 (purple) to pH 5.2 (yellow).

20 µl cell lysate was added to 180 µl of 1 mM sodium-phosphate buffer pH 6.0 supplemented with 0.5% acrylated hydroxypropylcarbamate and 60 µg/ml bromocresol purple in 96-well microtiterplates (MTP). The reaction progress was followed for 10 min by tracking the absorption abatement at 581 nm using a SpectraMax 386 PC MTP-spectrophotometer. After 10 min of measurement an image of the whole MTP displaying the activity-dependent color change was taken.

The same assay was used to characterize CALB variants expressed in *P. pastoris*. Therefore 1 ml PS cuvettes were used on a Pharmacia Ultrospec 3000 spectrophotometer.

Determination of Enantioselectivity 3 ml supernatant of CALB from expression in *P. pastoris* was mixed with 3 ml 100 mM sodium phosphate buffer with pH 7.5, and 44.25 µl 1-phenylethylpropionate was added in the mixture. Samples were taken at different times and were extracted by 300 µl isooctane respectively. After 1 min centrifugation at 14000 rpm 200 µl organic phase containing enantiomers of ester and ethanol was dried by $Na_2SO_4$ respectively and then analyzed directly on a Fisons instruments GC 8000 series.

Immobilization of CALB

As lyophilized CALB showed no conversion of the substrates, CALB was immobilized for the reaction.

Acrylation of Hydroxypropylcarbamate on Lab Scale

The transesterification of methylacrylate with hydroxypropylcarbamate was catalyzed by immobilized CALB. 500 µl hydroxypropylcarbamate (mixture of four stereoisomers primary:secondary alcohol) were converted with 12 ml methylacrylate (134 mmol) and 20 mg immobilized CALB in a 25 ml flask at 40° C. The reaction product methanol was removed from the reaction by addition of 3 g molecular sieve to shift the reaction equilibrium to the products.

Acrylation of Hydroxypropylcarbamate (Scale Up)

The transesterification of ethylacrylate with hydroxypropylcarbamate was catalyzed by immobilized CALB. 437 g hydroxypropylcarbamate (mixture of four stereoisomers primary:secondary alcohol) were converted with 3156 g Ethylacrylate and 35 g immobilized CALB at 40° C. The reaction product ethanol was removed from the reaction by distillation to shift the reaction equilibrium to the products.

GC/MS-Analysis

To analyze the transesterification reactions, samples were analyzed on a Shimadzu GC/MS-QP2010 equipped with a 30 m FS-Supreme column (internal diameter 0.25 mm, film thickness 0.25 µM) using helium as carrier gas at a linear velocity of 30 cm s$^{-1}$. The column oven was programmed as follows: 1) 40° C. for 1 min 2) 40 to 250° C. at 15° C. min$^{-1}$ 3) 10 min at 250° C. 4) 250 to 300° C. at 30° C. min$^{-1}$ 5) 300° C. for 1 min MS-settings were: interface at 270° C., ion source at 200° C., MS-scan frequency (TIC-mode) 2 s$^{-1}$.

Determination of Enantioselectivity

For determination of enantioselectivity hydrolysis of phenylethylpropionate was performed. Enantiomers of substrate and product were separated on a Fisons instruments GC 8000 series equipped with a 50 m cyclodex β-F/P column using $H_2$ as carrier gas. The column oven was programmed as follows: 1) 100° C. for 40 min 2) 100° C. to 175° C. at 10° C. min$^{-1}$. Retention times of phenylethylpropionate enantiomers were: (+) 46.8 min, (−) 47.1 min; Retention times of phenylethanol enantiomers were: (+) 40.7 min, (−) 42.7 min.

Assay Development and Validation

In order to screen mutant libraries and for characterization of individual mutants, an assay based on hydrolysis of the acrylated hydroxypropylcarbamate was developed. Protons released in the reaction are detected using the pH-indicator bromocresol purple. This setup allows online monitoring of the reaction progress. In order to validate the assay CAL-B_WT was expressed in Origami B in MTPs as described previously [Liu, 2006] and the assay reaction was performed. Using different amounts of CALB in the reactions showed that the slope is in proportion to the amount of CALB used in the respective well or cuvette. This system was in the following used to screen mutant libraries and for characterization of mutants expressed in *P. pastoris*.

Mutagenesis at Position L278

In order to determine and compare the activity of CALB mutants at position 278, the respective mutations were introduced by site-directed mutagenesis. The protein variants were expressed in *P. pastoris*. The results are summarized in table 3.

TABLE 3

Activity of different CALB mutants expressed in *P. pastoris* in tributyrine hydrolysis.

| CALB variant | WT | L278A | L278V | L278Y | L278F |
|---|---|---|---|---|---|
| Activity in tributyrine hydrolysis [U/mg] | 740 | 4390 | 1700 | 710 | 2630 |

Especially substitution of L278 by alanine had a dramatic effect on activity. Activity in hydrolysis of tributyrine is enhanced about 6-fold compared to wt.

Having achieved these encouraging results regarding tributyrine hydrolysis, the activity in the transesterification reaction of hpc with acrylic acid methyl ester was compared.

The mutants were immobilized on MP1000 and used in the transesterification reaction of hpc with acrylic acid methyl ester. The best mutant was found to be L278A, which displayed 97% conversion after 6 hours of reaction compared to WT displaying only 84% conversion after 24 hours. This result was confirmed by comparing the rate of hpca hydrolysis for WT and L278A. As displayed in Table 4, L278A shows about tripled hydrolysis rate for hpca compared to WT. A negative control using the empty pColdIII vector showed no detectable activity. Here no specific activities can be given as expression of CALB in E. coli leads only to low levels of active CALB. Therefore in the next step enzyme variants were expressed in P. pastoris. In these expression system high protein amounts in high purity can be obtained. This allows more accurate mutant characterization.

TABLE 4

Hydrolysis of hpca by CALB_WT compared to negative control and CALB_L278A. Measurements were performed in presence of the pH indicator bromocresol purple allowing tracking of the reaction progress at 581 nm.

|  | pColdIII | pColdIII/calb_wt | pColdIII/calb_L278A |
|---|---|---|---|
| V ($\Delta A_{581}{}^{s-1}$) | 2 | 28 | 76 |

Still it was obvious in preparative acrylation reactions that the reaction rate even with L278A declined over time. As the enzymatic activity was stable (proven by reuse of the lipase), this reaction-time dependent decline in rate is a result of the low activity of CALB WT and L278A towards the S-enantiomer of secondary alcohols.

In order to improve the enzymatic activity of this CALB-mutein we focused on position 104. In order to discover the best combination of mutations at positions 278 and 104, multi site saturation mutagenesis at these two positions was performed. Sequencing of 20 clones out of a library comprising 1400 members revealed that in both positions 90% of the plasmids carried the respective mutations.

Screening Result

A library comprising 1400 clones of the abovementioned mutant library was screened using the newly developed assay. The mutant L278A again showed highest activity (FIG. 1) in the hydrolysis of acrylated hydroxypropylcarbamate (hpca). Additionally the double mutant L278A W104F performed better than WT in the hydrolysis assay. This mutant was selected for further characterization as the reaction rate in the assay stayed stable for 30 min indicating decreased stereoselectivity and thus conversion of all substrate enantiomers. In contrast reactions using L278A showed a pronounced decrease of reaction rate within 30 min (FIG. 1). After 30 min the endpoint (color change from purple to yellow) for both mutants was about the same. WT shows only low activity in the assay. Due to the low reaction rate in the WT reactions, time-dependent decrease of reaction rate due to decreasing concentration of the preferred stereoisomer can not be detected. This interpretation is supported by the fact that conversion of substrate by WT reaches only half of the value obtained with mutants L278A and L278A W104F.

TABLE 5

Characterization of CALB mutants expressed in P. pastoris.

| CALB mutant | Activity in tributyrine hydrolysis (U mg$^{-1}$) | Activity in hydrolysis of hpca ($\Delta A_{581}$ min$^{-1}$ mg$^{-1}$) | Enantioselectivity (E) in hydrolysis of phenylethylpropionate |
|---|---|---|---|
| WT | 740 | 89 | >300 |
| L278A | 4390 | 195 | 200 |
| W104F | 250 | 26 | 30 |
| S47A | 850 | 64 | >300 |
| L278A W104F | 1770 | 130 | 4 |
| L278A S47A | 1100 | 207 | 80 |
| L278A W104F S47A | 5530 | 223 | 5 |

The activities of the mutants L278A, L278A W104F, L278A S47A and L278A W104F S47A is increased compared to the wild type. Interestingly the enantioselectivity is decreased in most of these mutants. Therefore increased activity can be attributed to more efficient conversion of the secondary alcohol's (S)-enantiomer. The mutants L278A W104F and L278A W104F S47A show a decreased stability compared to WT and mutant L278A The effects of combination of mutations at position 278 (responsible for increased activity) and 104 (responsible for decreased stereoselectivity) are additive (table 5). In contrast the effect of mutagenesis at position 47 is strongly dependent on the amino acids at positions 104 and 278. For example the single mutant S47A performs worse than WT in the hpca hydrolysis assays. On the other hand combination of S47A with L278A and W104F leads to a strong increase in hydrolysis activity towards hpca.

Activity in Acrylation of Hydroxypropylcarbamate

In order to measure the activity of mutants in the acrylation of hydroxyalkylcarbamates (FIG. 1), the respective mutants were immobilized on MP1000 and time-dependent conversion to the products was analyzed by GC measurements. Immobilization of CALB was necessary for the acrylation of hydroxypropylcarbamate, because without immobilization no measurable activity was observed. After immobilization CALB also showed increased activity in the hydrolysis of tributyrine compared to free enzyme.

Activity of Immobilized CALB in Acrylation of Carbamate-Alcohols

In the acrylation of hpc catalyzed by the mutant L278A or WT the mutant showed faster acrylation of hpc than the WT. Using WT yielded 84% conversion after 24 h while the mutant L278A led to 97% conversion after 6 h. Immobilization lead to increased specific activity of CALB WT and L278A in the acrylation of hpc.

Immobilization of the CALB Wildtype (SEQ ID NO:2) and CALB-Muteins

Material:
Carrier: Diaion HP20L (Fa. Resindion), not dried
Enzyme: CALB wildtype oder mutein (received from ultrafiltration)
The concentrate received from ultrafiltration was adjusted with $KH_2PO_4$ to a concentration of 50 mM pH 7.0.
The carrier was loaded with 5% of protein (weight protein/weight of undried carrier).

The protein was dissolved in 50 mM Phosphate pH 7.0 (end volume 100 ml for 10 g of carrier), shaken for 3.5 h (Stuart rotator drive STR 4) at 6° C.

The loaded carrier was filtered and washed with phosphate, the pellet was dried at room temperature.

Determination of Stereoselectivity of CALB Muteins vs CALB Wildtype

Reaction Conditions 150 mM 2-rac-hexanol and 50 mM dodecane in ethylacrylate. 2 ml of the solution is catalyzed with 25 mg immobilized enzyme. Samples were taken at different times, filtered and diluted in MTBE. Thereafter derivatized with Trifluoro acetic anhydride (1:3) at 100° C. for 30 min.

Analysis

GC for 2-hexanol

The samples were analyzed on GC equipped with 25 m Hydrodex-®-TBDAc; 0.255 mm ID; 0.25 μm FD, using He as carrier gas. 1 μl was injected at 250° C., oven program 50° C. for 15 min, 2° C./min to 180° C.

| Catalyst | U/mg | E-value |
|---|---|---|
| uncat | insignificant | |
| WT | 1282 | 527 |
| S47A | 1289 | 531 |
| T42A/S47A | 1090 | 241 |
| W104F/L278A | 1381 | 16 |
| L278A | 1863 | 196 |
| L278V | 1413 | 219 |

GC for HPC (Used for the Scaled Up Reaction, Instead of GC/MS-Analysis)

The samples were analyzed on GC equipped with 25 m Optima d6 GC6, using He as carrier gas. 1 μl was injected at 280° C., oven program 60° C. for 0 min, 15° C./min to 280° C. and kept for 10 min.

FIG. 1 shows the results of screening the mutant library W104X L278X. Mutants L278A and L278A W104F show the highest activities.

The invention claimed is:

1. A modified protein having acrylation activity wherein SEQ ID NO: 1 or SEQ ID NO:2 is modified by introducing at least one of the following amino acid substitutions selected from the group consisting of L278A, L278V, W104F, T42A and S47A.

2. The protein as claimed in claim 1, wherein the polypeptide sequence has two of the amino acid substitutions.

3. The protein as claimed in claim 1, wherein the polypeptide sequence has three of the amino acid substitutions.

4. A process for transesterification, wherein a stereoisomer mixture of an optically active alcohol of the formula II is contacted with an ester of the formula I in the presence of the protein as claimed in claim 1 and the acrylated mixture of alcohols of the formula III is obtained from the reaction medium,

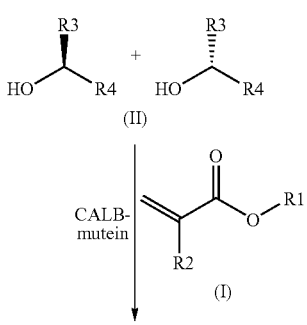

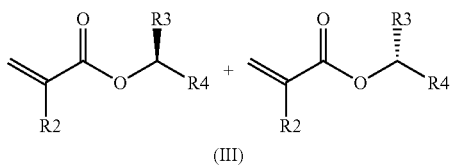

With $R^1 = C_1$-$C_6$ Alkyl $R^2 =$ H, $CH_3$ $R^3$, $R^4 = C_1$-$C_6$ Alkyl, where one or two H-atoms can be substituted by OH, SH, $NH_2$, F, Cl, Br, J, CN, —O—$CONH_2$, —O—COOH, —OCOOR$^1$, or aryl, with the proviso that $R^3 \neq R^4$.

5. The method as claimed in claim 4, wherein the ester of the formula I is Methylacrylate.

* * * * *